United States Patent [19]

Dow et al.

[11] Patent Number: 4,649,925
[45] Date of Patent: Mar. 17, 1987

[54] ULTRASONIC TRANSDUCER PROBE DRIVE MECHANISM WITH POSITION SENSOR

[75] Inventors: Julian Dow, San Clemente; Paul F. Meyers, San Juan Capistrano, both of Calif.

[73] Assignee: Technicare Corporation, Cleveland, Ohio

[21] Appl. No.: 691,320

[22] Filed: Jan. 14, 1985

[51] Int. Cl.⁴ .............................................. A61B 10/00
[52] U.S. Cl. ...................................... 128/660; 73/620
[58] Field of Search .................... 128/660; 73/618–620

[56] References Cited

U.S. PATENT DOCUMENTS

| | | |
|---|---|---|
| 3,741,004 | 6/1973 | Posakony .............................. 73/620 |
| 4,094,306 | 6/1978 | Kossoff ........................... 128/660 X |
| 4,130,022 | 12/1976 | Goodrich et al. ............... 128/660 X |
| 4,375,818 | 3/1983 | Suwaki et al. ....................... 128/660 |
| 4,407,293 | 10/1983 | Suarez, Jr. et al. ................. 128/660 |
| 4,421,118 | 12/1983 | Dow et al. ........................... 128/660 |

Primary Examiner—Kyle L. Howell
Assistant Examiner—Francis J. Jaworski
Attorney, Agent, or Firm—W. Brinton Yorks, Jr.

[57] ABSTRACT

An ultrasonic transducer probe is provided, in which the transducer is oscillated by a crank shaft for sector scanning. The crank shaft is driven by a motor having a moving magnet stack assembly in a tubular set of electromagnetic coils. The motor also moves a bimetallic pin through a position sensor coil so that the position of the transducer is represented by the detected inductance change of the coil.

2 Claims, 3 Drawing Figures

ULTRASONIC TRANSDUCER PROBE DRIVE MECHANISM WITH POSITION SENSOR

This invention relates to ultrasonic transducer probes for use in ultrasonic diagnostic imaging and, in particular, to drive mechanisms with transducer position sensors for use in such probes.

Transducer probes for ultrasonic imaging are designed to be small, light, and easy to manipulate for the production of real-time images of the internal tissue structure of a patient. In order to produce real-time images, beams of ultrasonic energy must be rapidly transmitted into the patient and echoes received by the probe for rapid processing in an imaging format suitable for display. It is generally desirable for the probe to be small, but also capable of imaging over a wide field of view that is greater than the probe aperature, with good image resolution. These conflicting requirements may be resolved by sweeping, or scanning, a number of ultrasonic beams in different directions, producing a so-called sector scan. There are in general two ways of doing this. One is to use a transducer with a linear array of elements, which can be excited in a phased relationship to "steer" beams of ultrasonic energy in radially different directions. Phasing is then also necessary during the reception of echo information, so that the received signals will be coherent in the selected direction of each transmission. This electronic beam steering technique, however, requires a great deal of complex electronics to direct the beam in the different directions, and to process the received echo information. The second technique is to mechanically move the transducer through an arc, thereby transmitting and receiving ultrasonic energy along a number of different radial directions. Desirably, the mechanism required to oscillate the transducer, and the associated drive and control electronics, are considerably simpler and less costly than the electronics of a phased array beam steering system.

In accordance with the principles of the present invention, a drive mechanism is provided for oscillating a pivotally mounted transducer through a given arc of travel. The mechanism comprises a linear motor connected to a crank shaft. The other end of the crank shaft is connected to the transducer assembly at a point which is offset from the axis about which the transducer pivots. The linear motor moves the crank shaft in a reciprocating manner, which correspondingly oscillates the transducer through an arc about its pivot axis.

Linear motors of this type are constructed of two primary portions: a permanent magnet portion and an electromagnetic portion. The electromagnetic portion is driven with a signal which generates a changing electromagnetic field. The magnetic field emanating from the permanent magnet then interacts with the changing electromagnetic field, thereby producing relative motion between the two portions.

In ultrasonic transducer probes, it is desirable for the moving motor portion to have low mass. Moving a low mass motor portion results in the generation of small vibrational characteristics in the probe. This is desirable, so that the user will not sense any probe vibrations as the probe is held against or moved across the patient. Ideally, the probe should generate no vibrations whatsoever. Accordingly, the conventional wisdom is that, since the permanent magnet is generally more massive than the electromagnet, it is the electromagnet that should be the moving member, while the permanent magnet is held stationary. Such a philosophy is exemplified by the transducer probe motor shown in U.S. Pat. No. 4,421,118.

However, the conventional wisdom does not fully consider the fact that a permanent magnet can exhibit up to ten times the magnetic flux of an electromagnetic coil of the same weight. In order to take full advantage of this relationship in the design of a motor used to oscillate a transducer of appreciable size through a viscous liquid, it is necessary to increase the windings of the electromagnetic coils. The electromagnet, by reason of its relatively lower flux to weight relationship, then soon becomes sizeable, which increases the size of the motor and hence the dimensions of the probe.

In accordance with a further aspect of the present invention, the permanent magnet of the motor is used as the motive means for oscillating the transducer. The power to be delivered by the motor is then selected during design by increasing or decreasing the number of turns of the electromagnetic coils, thereby taking advantage of the relatively large magnetic flux exhibited by the permanent magnet. An increase in the number of turns will increase the diameter of the motor, which is generally tolerable, but will not increase its length, a desirable characteristic. A motor of relatively short length permits the location of other components in the probe for the transducer assembly, position sensor and electrical connections without the need to excessively lengthen the probe. Moreover, a motor can be redesigned to provide more or less power without altering the inertial characteristics of its motive member, since the magnet may generally be left unchanged. Furthermore, as an electromagnet is moved, the wires connecting it to its drive circuit are caused to repeatedly flex. This poses a reliability problem, as the flexing wires can break over time. This inherent problem in the moving electromagnet motors is avoided in the present invention.

An indispensable characteristic of an oscillating transducer probe is the necessity of knowing the angular position of the transducer each time it transmits and receives ultrasonic energy. Without this ability, the coordination of echo information with location cannot be performed, and a positionally accurate image cannot be formed. In accordance with another aspect of the present invention, the motive permanent magnet of the probe motor moves a metallic pin through a coil as it oscillates the transducer. The movement of the pin through the coil changes the inductance of the coil, which change is detected by a position sensor circuit and used to develop positional information used in the production of an ultrasonic image. In the preferred embodiment of the present invention, the pin is bimetallic, with one portion of the pin being composed of a metal which increases the inductance of the coil, and a second portion composed of a metal which decreases the inductance of the coil. The use of a pin of these characteristics results in the development of a wider range of inductance variation than would otherwise be obtained through use of a pin composed of a single material.

Figure 1:
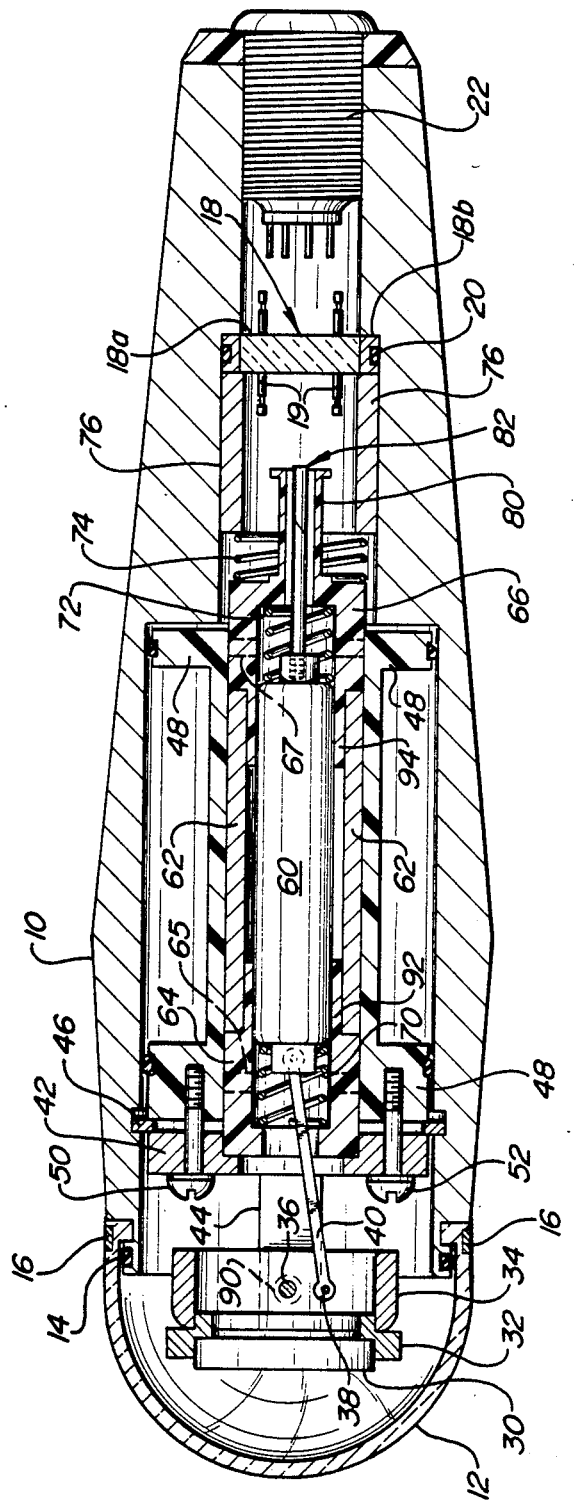
FIG. 1 illustrates a partially cross-sectional view of an ultrasonic transducer probe constructed in accordance with the principles of the present invention.

Referring first to FIG. 1, an ultrasonic transducer probe constructed in accordance with the principles of the present invention is shown. The probe elements are housed in a case 10, which may be made of aluminum, delrin, polysulfone or similar material. An acoustic cone or cap 12 is fitted at the end of the case. The cap 12 is made of polyethylene or other material which is highly transmissive to ultrasound. During use, ultrasonic energy passes through the cap 12 to and from an ultrasonic transducer 30 by way of the intervening fluid inside the probe. The acoustic cap 12 is fitted into a groove around the periphery of the open end of the case, and is held in place by a compression band 16. This seal is made fluid-tight by an O-ring 14 compressed between the cap 12 and the case 10.

The transducer 30 is seated in a transducer ring 32. The transducer ring 32 then snaps into place in a transducer cup 34. This permits the manufacture of a variety of transducers of different characteristics in transducer rings of the same outer dimension. When a customer orders a probe with a specified transducer, the selected transducer and ring module can be snapped into the transducer cup with the necessary electrical connections being made. The finished probe can then be inspected and sent to the customer.

The transducer cup 34 contains ball bearing fittings on either side, with a hard steel axle pin 36 passing therethrough. A stainless steel crank pin 38 is press fit through the transducer cup parallel to the axle pin 36. In a constructed embodiment of the present invention, the crank pin 38 is spaced apart from the axle pin 36 by a distance of 0.090 inches. This spacing is one of the determining factors of the angle through which the transducer is oscillated. In the constructed embodiment, the oscillation angle was 90 degrees. It was found that a one thousandth of an inch variation in the spacing distance corresponded to a one degree variation in the oscillation angle.

One end of a crank shaft 40 is connected to the crank pin 38 in a bearing fit. The other end of the crank shaft 40 is connected to the moving magnet assembly 60 of the motor, also in a bearing fit. The ends of the axle pin 36 which extend from the transducer cup 34 are located in holes in the arms 44 which extend from the base of a gimbal cup 42. The axle pin is held firmly in the holes in the gimbal cup arms by orthogonally directed set screws in the gimbal cup arms. The gimbal cup is held in place in the probe by screws 50 and 52, which pass through holes in the gimbal cup and into threaded holes in an expansion bushing 48, which loosely surrounds the motor. The base of the gimbal cup and the spool-shaped expansion bushing thereby sandwich a snap ring 46, which extends around the inner circumference of the case 10. This technique of construction is more fully described in concurrently filed U.S. patent application Ser. No. 691,319 filed Jan. 14, 1985, entitled "ULTRASONIC TRANSDUCER PROBE ASSEMBLY."

An upper bearing 64 of the motor is fitted at one end into a groove in the base of the gimbal cup 42. A lower bearing 66 is held in place by a shock mounting spring 74 and a tube 76, the latter contacting a glass/metal seal 18. The inner portion 18a of the seal is made of glass, and has a number of electrical connection pins 19 passing through it. Leads from the transducer, the motor and the position sensor (not shown) are connected to these pins. The outer periphery 18b of the seal is made of metal, and is surrounded by an O-ring 20. This O-ring 20 forms a fluid tight seal at the back of the probe, and terminates the fluid compartment in which the motor and transducer assembly are located. Connections are then made between the connection pins on the outside of the fluid compartment and a connector 22. The connector 22 may then be mated with a corresponding plug on the end of a cable, thereby bringing the necessary signals to and from the probe.

The crank shaft 40 passes through holes in the center of the gimbal cup 42 and the upper bearing 64, and is connected to the magnet assembly 60. The magnet assembly slides in a reciprocating manner in the bearings 64 and 66, which are made of delrin. Compression springs 70 and 72 are located at either end of the magnet assembly, and serve to locate the magnet assembly in a central position of the motor when the motor is not operating. In this position, the transducer is located facing directly ahead, as shown in the drawing. The compression springs 70, 72 also assist the motor at turnaround, the times at which the magnet assembly 60 is reversing its direction of travel. The cylindrical magnet assembly 60 is surrounded by a tubular coil assembly 62. A position sensor pin 82 is screwed into a threaded hole at the lower (right hand) end of the magnet assembly. As the coil assembly 62 is energized, the magnet assembly 60 moves back and forth, or horizontally in the drawing. The crank shaft 40 is thereby reciprocated back and forth, which moves the transducer cup and transducer in oscillatory fashion about the axle pin 36. At the same time, the magnet assembly moves the position sensor pin 82 through a position sensor coil form 80, which is formed as a part of the lower bearing 66. A coil is wound around the coil form 80 (shown in FIG. 3), and the movement of the position sensor pin 82 through the coil changes the inductance of the coil in relation to the location of the pin and correspondingly the angular orientation of the transducer. This changing inductance is sensed and used to establish the instantaneous position of the transducer.

Figure 2:
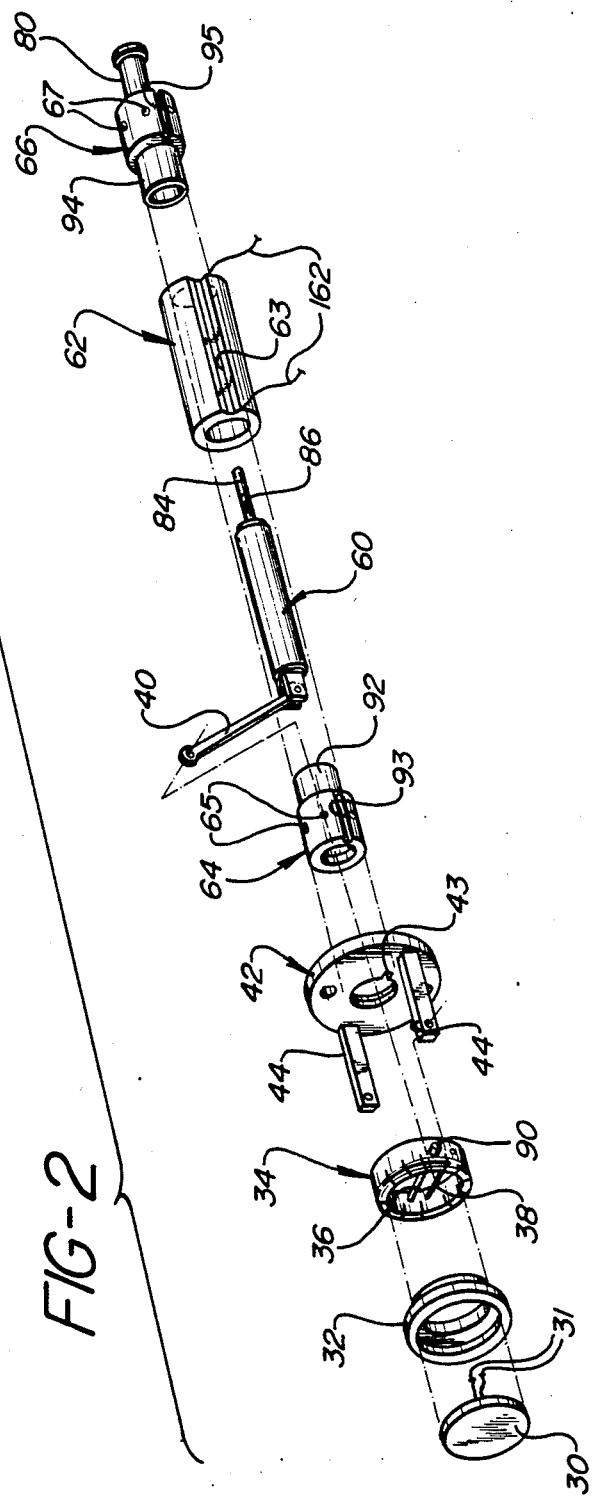
FIG. 2 illustrates an assembly drawing of the major elements of the transducer drive mechanism of the probe of FIG. 1.

Referring to FIG. 2, an assembly drawing of the major elements of the transducer drive mechanism of the probe of FIG. 1 is shown. At the left of the drawing is the transducer 30. The wires 31 connected to the back of the transducer are routed through the probe to the connection pins 19 at the back of the probe fluid chamber. The wires 31 pass through the transducer ring 32 and the transducer cup 34 into a notch 43 in the inner circumference of the gimbal cup 42. This notch 43 is aligned with a groove 93 in the upper bearing 64, a groove 63 in the coil assembly 62, and a groove 95 in the lower bearing 66. From there the wires pass through the space at the lower end of the motor to the connection pins 19. In the coil assembly groove 63 and the lower bearing groove 95 the transducer wires 31 are accompanied by wires 162 of the coil assembly 62.

The transducer 30 is fitted into an annular groove of the transducer ring 32. This groove contains a coating of a resilient, soft rubber material. By seating the transducer in soft rubber, ultrasonic transmission into the transducer ring is largely prevented, which minimizes the generation of reverberation and its image artifacts in the probe.

The transducer ring 32 snaps into the transducer cup 34. The front of the transducer cup is slotted approximately every twenty degrees around the ring to allow the snap fit. The axle pin 36 is shown passing through the transducer cup, where it is seated in ball bearing fittings, one of which is indicated at 90. The crank pin 38 is securely press fit into the transducer cup.

The ends of the axle pin 36 fit into the holes in the sides of the arms 44 of the gimbal cup 42. At the tips of the arm 44 can be seen the holes for the set screws used to hold the axle pin securely in place.

The upper bearing 64 and the lower bearing 66 are also shown in FIG. 2. Around the periphery of the larger diameter portion of the bearings are a number of holes 65 and 67 which pass through the bearings. These holes vent fluid between the insides of the bearings at either end of the moving magnet assembly 60 and the outside of the motor. The motor fits loosely inside the expansion bushing 48, thereby creating a small, fluid-filled space between the inner surface of the expansion bushing 48 and the outer surfaces of the bearings and the coil assembly 62. As the magnet assembly moves back and forth, it effects a pumping action on the fluid within the motor. Without some way of venting the fluid, the motor could experience a binding effect due to the pressure of the fluid within the motor. The holes 65, 67 prevent this potential binding problem.

The smaller diameter extensions 92 and 94 of the bearings provide bearing surfaces in their interiors for the moving magnet assembly 60. These extensions 92 and 94 fit inside the ends of the coil assembly 62.

Figure 3:
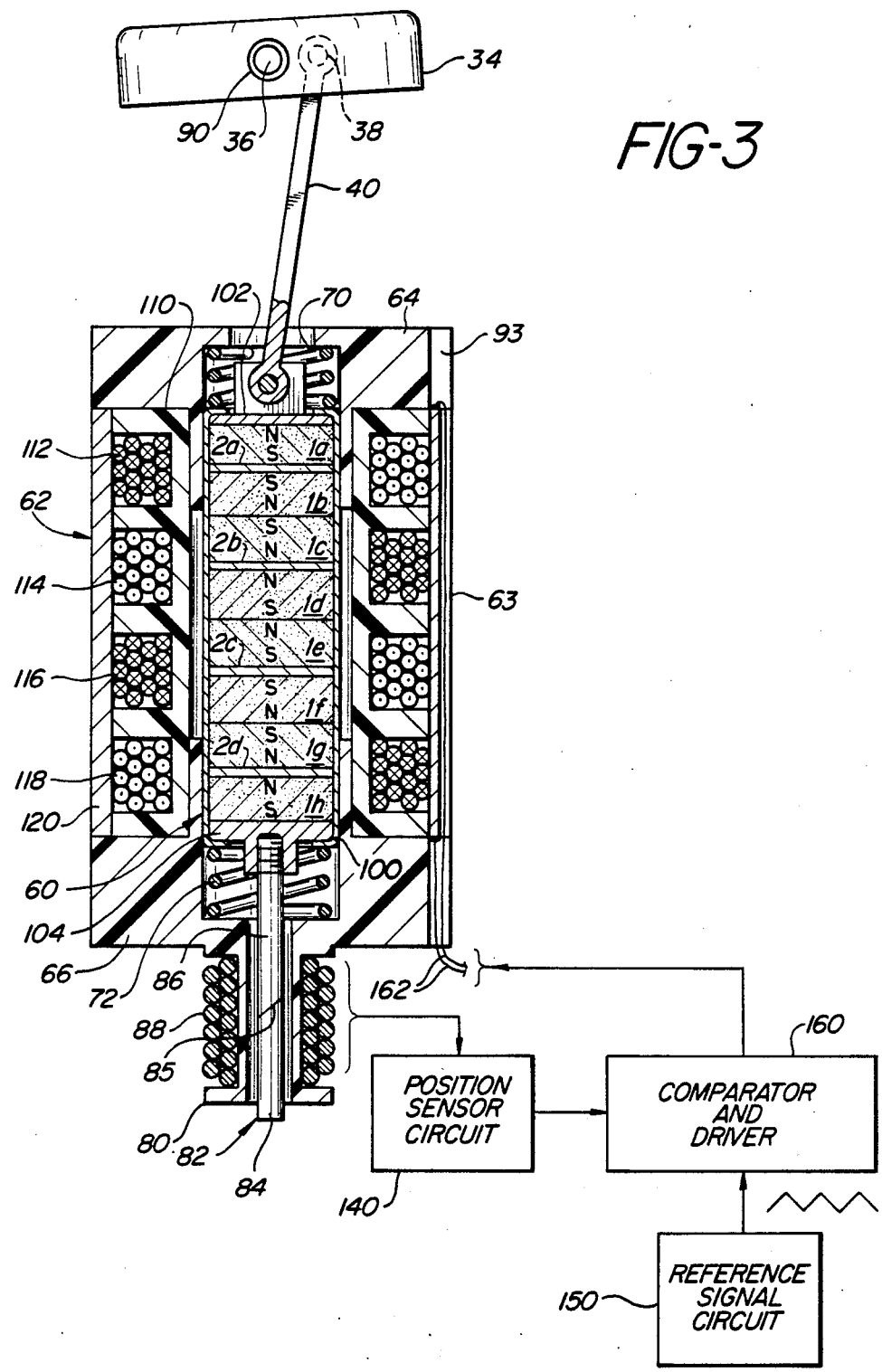
FIG. 3 illustrates, partially in cross-sectional representation and partially in block diagram form, the motor and control mechanism of the present invention.

A more detailed cross-sectional view of the assembled motor and its control circuitry is shown in FIG. 3. The coil assembly of FIG. 3 is not drawn to scale so that the winding directions can be clearly shown. The illustrated bearings are also expanded in size to illustrate the alignment of grooves 93 and 95 (see FIG. 2) with the groove 63 in the coil assembly return tube. The motor is shown connected to the transducer cup 34 by crank shaft 40, with the transducer cup 34 pivoting around the axle pin 36. At the top of the magnet assembly the crank shaft 40 is connected to a brass drive bushing 102. At the bottom of the magnet assembly is a brass lower end bushing 104, threaded to receive the position sensor pin 82. Between the bushings 102, 104 are a number of samarian cobalt iron magnets 1a-1h, separated into pairs by permendur iron spacers 2a-2d. Each magnet pair has opposite poles in contact with each other, and each pair opposes an adjacent pair with a like polarity magnet pole. The end magnets 1a and 1h are unpaired in the illustrated embodiment.

The flux lines of the magnet pairs emanate outward toward the surrounding coil assembly 62 from the iron spacers. The spacers 2a-2d exhibit high magnetic permeability and high saturation flux so as to guide the flux lines radially toward the electromagnetic coil assembly.

The bushings 102, 104, the magnets 1a-1h, and the spacers 2a-2d are stacked as shown in the drawing in a stainless steel compression tube 100. The ends of the tube 100 are braised to a bushing at one end and rolled at the other end to compress the stack together. The non-magnetic tube 100 readily passes the flux lines between the magnet assembly and the surrounding electromagnetic coil assembly 62.

The coil assembly 62 includes an aluminum coil former 110 which locates the coil windings in four groups 112-118. The coil is a continuous winding of 600 turns of #36 magnet wire, with the turns distributed among the four groups. From group to group, the direction of the winding reverses, as indicated in the drawing. The wire 162 enters and exits the coil assembly at the top and bottom of the coil former 110.

Surrounding the coil former 110 and coils is a steel magnetic return tube 120. The return tube 120 forms a case around the motor, acts to keep the motor fields within the motor, and also acts to guide the magnetic flux lines at the outer periphery of the coils up or down, depending upon one's point of reference.

When the assembled motor is at rest with the magnet assembly centered in the coil assembly, the spacers 2a-2d are centered with respect to respective coil groups 112-118. As an a.c. energizing signal is applied to the motor, the magnet assembly is moved to positions above and below the centered position in accordance with the changing electromagnetic field. In a constructed embodiment of the present invention, only a relatively small range of travel of 0.15 inches is needed to oscillate the transducer through a 90 degree arc.

As the magnet assembly is moved up and down, it moves the position sensor pin up and down in the position sensor coil form 80. A coil 88 is wound around the coil form 80. The number of coil turns is dependent upon the desired delta inductance, or inductance change, which the coil is to exhibit as the position sensor pin is moved through it. The coil 88 is connected to a position sensor circuit 140, which senses this delta inductance.

In accordance with the principles of the present invention, the position sensor pin is bimetallic, with one metal effecting an increase in coil inductance and the other metal effecting a decrease in inductance. In the illustrated embodiment, the upper portion 86 of the pin is made of mild steel. As this portion of the pin moves into the coil, it increases the coil inductance. The lower portion 84 of the pin is made of aluminum, and is joined to the upper portion at an interface 85. As the pin moves upward and the lower portion 84 more fully occupies the inside of the coil, a decrease in coil inductance is effected. The range of travel of the position sensor pin is also 0.15 inches, with the interface 85 always remaining within the coil 88 in the illustrated embodiment. Hence, the "magnification" of the changing coil inductance by the bimetallic pin results in a greater delta inductance and thus more accurate position sensing than that obtainable from a pin made of a single material.

The position sensor circuit may be a conventional one, such as the linear voltage differential transformer (LVDT) circuits used in model airplane servo systems and the like. In the constructed embodiment of the present invention, a constant current 100 KHz sine wave signal is applied to the position sensor coil 88. The changing coil inductance modulates the voltage of this signal between about 0.75 volts and 1.25 volts. The envelope of the changing signal is detected by rectification, a.c. coupled to remove its D.C. component, and amplified to produce a position signal. The position signal is then applied to a comparator in a comparator and driver circuit 160, where it is compared with a triangular reference signal produced by a reference signal circuit 150. The result of this signal comparison is used by the comparator and driver circuit 160 to develop a suitably timed a.c. drive signal for the coil of the motor. In general, the transducer's angular position will be a function of the angle of the a.c. driving voltage, with a small phase lag. The servo system will continually drive the motor to track the triangular reference signal. In a constructed embodiment, the a.c. drive signal is substantially a constant current signal in a range of 2-4 volts r.m.s., with a peak at turn-around of about 12 volts.

What is claimed is:

1. An ultrasonic transducer probe comprising:
   a transducer assembly:
   means for structurally mounting said transducer assembly within said housing;
   said transducer assembly further including a transducer located in a transducer cup, said transducer cup having a first pivot axis passing therethrough which is stationary with respect to said housing so as to direct beams of ultrasonic energy in a plurality of radially disposed directions through said acoustic aperture as said transducer and said transducer cup pivot about said first pivot axis;
   a motor, including a reciprocating member;
   means for structurally mounting said motor within said housing so that said transducer assembly is located between said motor and said acoustic aperture; and
   a single rigid connecting member having a first end pivotally connected to said reciprocating motor member and a second end connected to said transducer assembly at a second pivot axis located parallel to and offset from said first pivot axis, which second pivot axis is capable of movement about said first pivot axis for translating the reciprocating motion of said motor into pivoting motion of said transducer about an actual pivot axis.

2. The ultrasonic transducer probe of claim 1, wherein said connecting member comprises a crank shaft having one end pivotally connected to said reciprocating motor member, and the other end pivotally connected to said second pivot axis of said transducer assembly.

* * * * *